US009526457B2

(12) United States Patent
Li et al.

(10) Patent No.: US 9,526,457 B2
(45) Date of Patent: Dec. 27, 2016

(54) PREDICTIVE INTERVERTEBRAL DISC DEGENERATION DETECTION ENGINE

(71) Applicants: Shuo Li, London (CA); Sudhakar Tummala, London (CA); Kengyeow Tay, London (CA); Walter Romano, London (CA); Derek Ho, London (CA); Said Osman, London (CA)

(72) Inventors: Shuo Li, London (CA); Sudhakar Tummala, London (CA); Kengyeow Tay, London (CA); Walter Romano, London (CA); Derek Ho, London (CA); Said Osman, London (CA)

(73) Assignee: General Electric Company, Schenectady, NY (US)

( * ) Notice: Subject to any disclaimer, the term of this patent is extended or adjusted under 35 U.S.C. 154(b) by 60 days.

(21) Appl. No.: 14/591,017

(22) Filed: Jan. 7, 2015

(65) Prior Publication Data
US 2015/0201887 A1    Jul. 23, 2015

Related U.S. Application Data

(60) Provisional application No. 61/925,755, filed on Jan. 10, 2014.

(51) Int. Cl.
| | |
|---|---|
| *G06K 9/00* | (2006.01) |
| *A61B 5/00* | (2006.01) |
| *A61B 6/03* | (2006.01) |
| *G06F 19/00* | (2011.01) |
| *A61B 5/055* | (2006.01) |

(52) U.S. Cl.
CPC .......... *A61B 5/7275* (2013.01); *A61B 5/4514* (2013.01); *A61B 5/4566* (2013.01); *A61B 6/032* (2013.01); *G06F 19/321* (2013.01); *G06F 19/345* (2013.01); *G06F 19/3406* (2013.01); *A61B 5/055* (2013.01); *A61B 2576/02* (2013.01)

(58) Field of Classification Search
USPC ................ 382/100, 103, 106–107, 128–134, 154,382/162, 168, 173, 181, 199, 209, 219, 232,382/254, 274, 276, 286–291, 305, 320; 705/3; 424/1.11; 600/309, 340; 378/4, 21; 623/17.16
See application file for complete search history.

(56) References Cited

U.S. PATENT DOCUMENTS

| | | | |
|---|---|---|---|
| 2008/0097794 A1* | 4/2008 | Arnaud .................. | A61B 6/583 705/3 |
| 2011/0029084 A1* | 2/2011 | Milbocker .............. | A61F 2/442 623/17.16 |
| 2013/0053658 A1* | 2/2013 | Peacock ................. | A61B 5/055 600/309 |
| 2013/0230454 A1* | 9/2013 | Gardner ................. | A61K 38/18 424/1.11 |
| 2014/0081659 A1* | 3/2014 | Nawana ................. | G06Q 10/10 705/3 |

* cited by examiner

*Primary Examiner* — Seyed Azarian

(57) ABSTRACT

Systems, methods and computer program products for facilitating the prognosis of degenerative disc disorder (DDD) are provided. In one aspect, intervertebral disc loss is predicted based on receiving image data comprising one or more images of the human spine; segmenting, using a processor, disc regions of said one or more images; generating, using the processor, individual biomarkers based on texture features of said segmented disc regions; generating, using the processor, a predicting intervertebral disc loss based in part on the prognostic marker generated from the individual biomarkers.

15 Claims, 5 Drawing Sheets

PREDICTIVE INTERVERTEBRAL DISC DEGENERATION DETECTION ENGINE

CROSS-REFERENCE TO RELATED APPLICATIONS

This patent claims priority to U.S. Provisional Application Ser. No. 61/925,755, entitled "PREDICTIVE INTERVERTEBRAL DISC DEGENERATION DETECTION ENGINE," which was filed on Jan. 10, 2014 and is hereby incorporated herein by reference in its entirety.

FIELD OF THE DISCLOSURE

The present disclosure generally relates to automated prognosis of disease using medical images. In particular, the present disclosure relates to systems and methods for a predictive intervertebral disc degeneration detection engine.

BACKGROUND

The statements in this section merely provide background information related to the present disclosure and may not constitute prior art.

Degenerative disc disease or degenerative disc disorder (DDD) is a condition that can be painful and can greatly affect the quality of one's life. Disc degeneration is a disease of aging, and though for most people is not a problem, in certain individuals a degenerated disc can cause severe chronic pain if left untreated. Disc degeneration (i.e., loss) is one of the central processes in the pathogenesis of DDD. It is characterized by loss of water content, loss of disc nucleus and eventually reduction of disc height.

For any disease, the underlying pathophysiological processes may be related to the structural changes in tissues and therefore quantified as markers of diagnosis, progression and/or efficacy. Non-invasive assessment of spine has been possible with the existence and advancement of imaging techniques such as radiograph, magnetic resonance imaging (MRI), computed tomography (CT), Ultrasound, etc. Therefore, computer aided diagnosis (CAD) and computer aided prognosis (CAP) systems play a vital role in day-to-day life of radiologists by helping them to make better clinical decisions. While several grading systems are documented in the present day medical literature, there is currently no "gold standard" for the diagnosis of DDD other than the use of magnetic resonance imaging (MRI). An MRI enables a radiologist to visualize all the tissues present in a joint in 3D. Image texture is used extensively for disease diagnosis and prognosis. These texture markers provide means for CAD and CAP systems. In recent studies, combination markers developed from pattern recognition techniques showed better performance for diagnosis and prognosis.

BRIEF SUMMARY

This Summary is provided to introduce a selection of concepts. These concepts are further described below in the Detailed Description section. This Summary is not intended to identify key features or essential features of this disclosure's subject matter, nor is this Summary intended as an aid in determining the scope of the disclosed subject matter.

Aspects of the present disclosure meet the above-identified needs by providing systems, methods, and computer program products for facilitating the prognosis of DDD. In the present disclosure, image texture features quantified from images are used as biomarkers for prognosis of intervertebral disc loss, computed in the lumbar region of the spine. Thus, the present disclosure uses a grading system—similar to that used for magnetic resonance imaging (MRI)—to validate the ability of markers to diagnose DDD. The grading system is based on homogeneity of disc nucleus signals, combined with signal intensity of disc nucleus and annulus and disc height.

Figure 1:
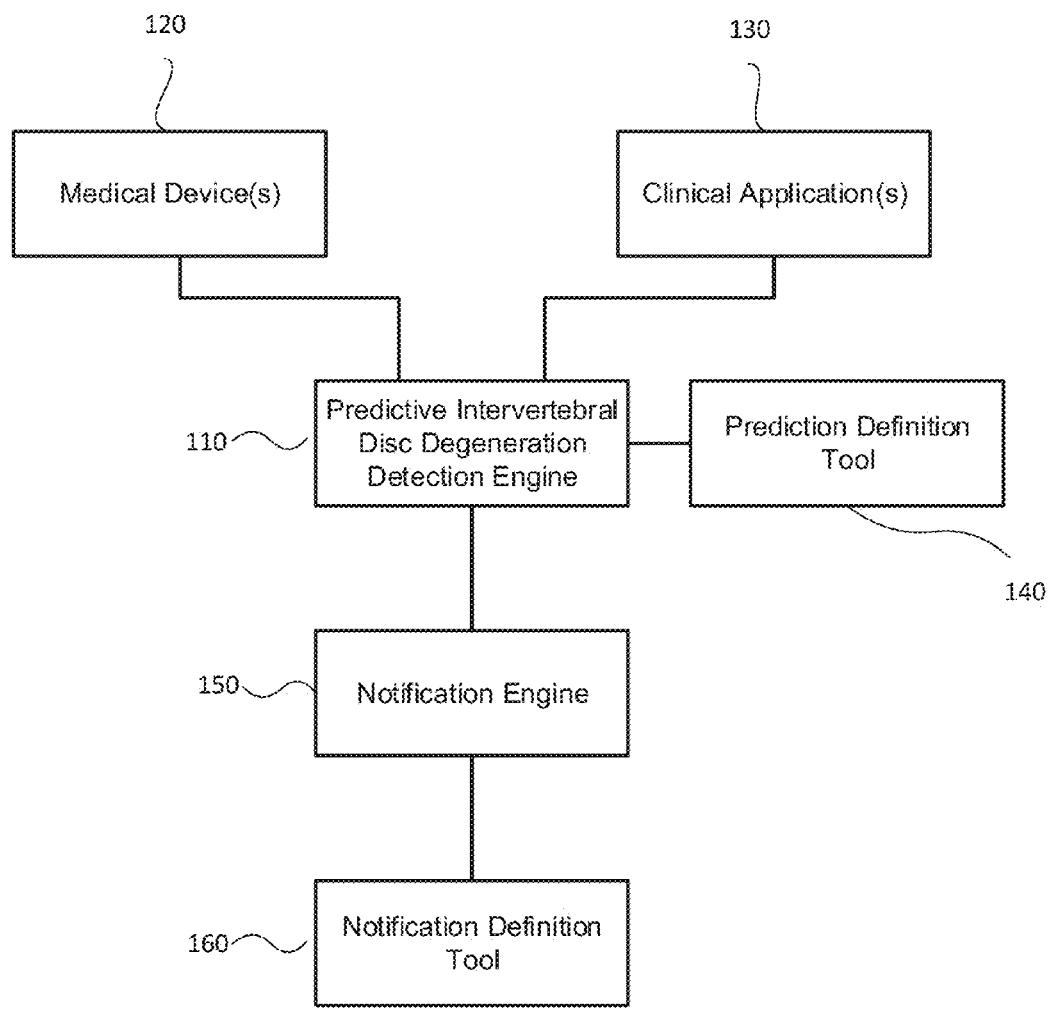
FIG. 1 illustrates a block diagram of a predictive intervertebral disc degeneration system according to an aspect of the present disclosure.

The foregoing summary, as well as the following detailed description of certain aspects of the present disclosure, will be better understood when read in conjunction with the appended drawings. For the purpose of illustrating the disclosure, certain aspects are shown in the drawings. It should be understood, however, that the present disclosure is not limited to the arrangements and instrumentality shown in the attached drawings.

DETAILED DESCRIPTION

Certain aspects of the present disclosure provide systems, methods and computer program products for a predictive intervertebral disc degeneration detection engine based on medical images, imaging biomarkers and/or patient information such as, for example, family history or previous symptoms. Certain aspects provide notification based on information from the predictive intervertebral disc degeneration detection engine.

FIG. 1 illustrates a block diagram of a predictive intervertebral disc degeneration detection system 100 according to an aspect of the present disclosure. System 100 includes a predictive intervertebral disc degeneration detection engine 110, one or more medical devices 120, one or more clinical applications 130, a prediction definition tool 140, a notification engine 150, and a notification definition tool 160. Engine 110 is in communication with the medical devices 120, the clinical applications 130, the prediction definition tool 140 and the notification engine 150. The notification engine 150 is in communication with the notification definition tool 160.

In operation, a medical device 120 generates data in the form of images or data values for a parameter. In addition, a clinical application 130 generates or retrieves clinical information data. Both sets of data are received by engine 110 which processes the data values based on a predictive algorithm to determine a prediction relating the prognosis of intervertebral disc degeneration. The predictive algorithm may be specified by a user using prediction definition tool 140. Based on the prediction, a notification is generated by notification engine 150.

In alternate aspects, medical device 120 may be one or more imaging devices, physiological monitors, electronic medical records or any like device able to provide data which can be used as a biomarker. A biomarker generally refers to a measured characteristic which may be used as an indicator of a biological state or condition. An imaging biomarker is a biologic feature, or biomarker detectable in an image that is often relevant to a patient's diagnosis.

In alternate aspects, clinical application 130 may be one or more devices or data stores which provide information such as family history information, previous symptom information, or other medical data. That is, clinical application 130 may be, for example, an order entry application, a pharmacy application, a medication management application, an electronic medical record and/or the like.

In an aspect of the present disclosure, engine 110 is adapted to determine a prediction based at least in part on the data received from medical devices 120 and/or clinical applications 130. Certain aspects of the present disclosure allow the prediction of intervertebral disc degeneration based on image texture features (imaging biomarkers) quantified from imaging techniques such as, for example, radiograph, MRI, CT or Ultrasound. In another aspect, the present disclosure allows for the prediction of intervertebral disc degeneration based on imaging biomarkers, non-imaging biomarkers and/or clinical data.

In an aspect of the present disclosure, engine 110 may determine a trend based on one or more of the aforementioned biomarkers or data elements. The predictive algorithm may, for example, utilize trending analysis and/or evaluating a trend over time. The predictive algorithm may determine the occurrence of an event at some point in the future. Based on this determination, notification engine 150 may provide a notification. For example, the predictive algorithm may determine that there is a trend that may lead to an intervertebral disc loss. Thus, detection engine 110 would then communicate with notification engine 150, which may notify a healthcare provider of this trend and timeframe.

In certain aspects, the predictive algorithm is specified by the user using prediction definition tool 140. For example, a user may utilize prediction definition tool 140 to create or develop a predictive algorithm to be provided to detection engine 110. Detection engine 110, in turn, may then execute the predictive algorithm based on the received biomarker data and, when indicated by the algorithm, provide a notification.

In one aspect, prediction definition tool 140 may allow the user to specify complex algorithms. In certain aspects, prediction definition tool 140 is adapted to allow for the creation and development of default standard-of-care predictive protocols. In certain aspects, prediction definition tool 140 is adapted to allow for the creation and development of patient-specific predictive protocols. In certain aspects, the prediction algorithm determines a prediction based at least in part on data from multiple parameters. These patient-specific protocols may be developed based on additional data that is discovered during patient care from one or more of medical devices 120, or as indicated by additional biomarkers or other data relevant to the patient's treatment gathered through traditional medical information means, such as through an electronic medical record (EMR) or other clinical applications 130.

In certain aspects, the prediction algorithm determines a prediction based at least in part on data from a clinical application 130. In certain aspects, the prediction algorithm determines a prediction based at least in part on data from multiple clinical applications 130. In certain aspects, the prediction algorithm determines a prediction based at least in part on data from at least one clinical application 130 and at least one medical device 120. In certain aspects, notification engine 150 is adapted to generate a notification based on the determined prediction. For example, the notification may be an email to a healthcare provider treating a patient, a message sent to an alert inbox of a physician, a page, text message, a telephone message and/or the like.

Figure 2:
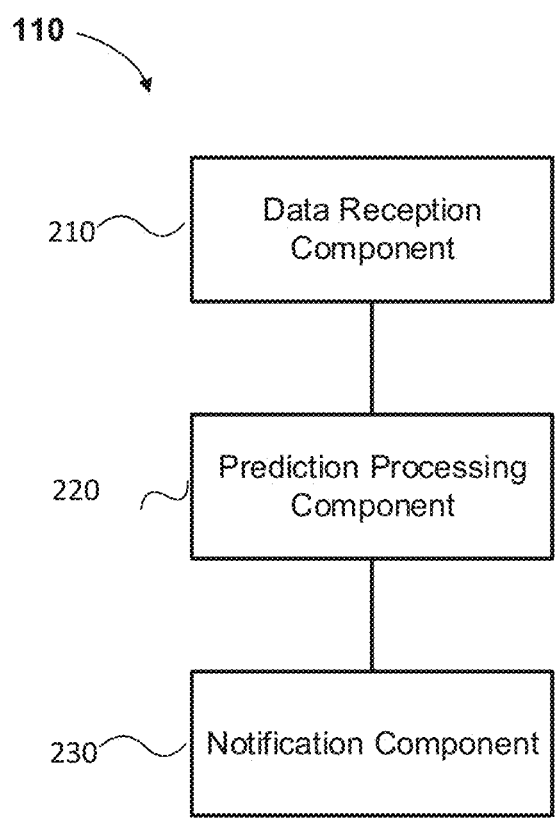
FIG. 2 illustrates a block diagram for a subset of a predictive intervertebral disc degeneration system according to an aspect of the disclosure.

FIG. 2 illustrates a block diagram for an intervertebral disc degeneration detection engine 110 according to an aspect of the present disclosure. In one aspect, the intervertebral disc degeneration detection engine 110 includes a data reception component 210, a prediction processing component 220, and a notification component 230. The prediction processing component 220 is in communication with the data reception component 210 and the notification component 230.

In operation, the data reception component 210, receives a sequence of data values for a parameter from a medical device 120. These data values can be either simple data values or in the form of image data. The data reception component 210 provides the parameter values to prediction processing component 220. Prediction processing component 220 processes the parameter values to determine a prediction. Based on the prediction, prediction processing component 220, may utilize the notification component 230 to generate a notification.

The data reception component 210 is adapted to receive a sequence of data values for at least one parameter. The data values may come from one or more medical devices 120. In certain aspects, the data component is adapted to receive data from one or more imaging devices or applications. In certain aspects, the data component is adapted to receive data from one or more clinical applications 130.

In certain aspects, data reception component 210 receives data from a clinical application 130 such as a data records server. That is, data reception component 210 may receive data from an intermediate data storage infrastructure in an information system such as a clinical information system, a healthcare information system and/or a picture archiving and communication system (PACS). In each instance, the data may be recently-added to the clinical data records server or may have been previously-stored for later analysis and/or review.

Prediction processing component 220 is adapted to determine a prediction based at least in part on the parameter values received by data reception component 210. The prediction may be determined by, for example, a predictive algorithm. For example, prediction processing component 220 may include a predictive algorithm that is executed when parameter data is received from data reception component 210. The predictive algorithm may determine a trend based on one or more parameters. The predictive algorithm may then determine that at some point in the future, the determined trend would indicate the occurrence of an event. Based on this determination, prediction processing component 220 may utilize notification component 230 to generate a notification.

Notification component 230 is adapted to generate a notification based on a prediction from prediction processing component 220. Notification component 230 may provide a notification to a clinical information system, a healthcare information system, a healthcare provider and/or the like. In certain aspects, a notification is stored in a clinical server. The stored notification may be used for auditing, playback, etc.

Figure 3:
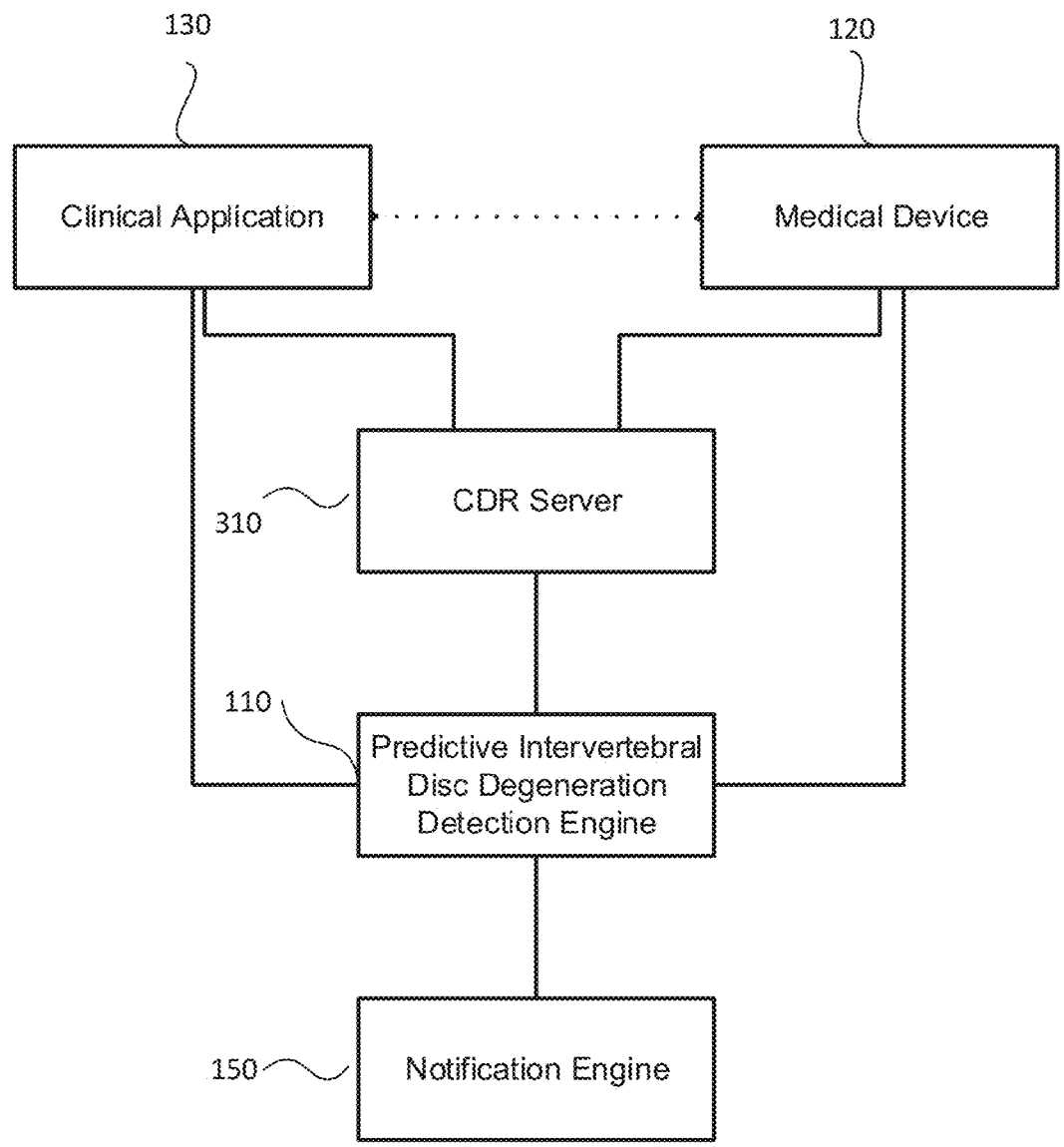
FIG. 3 illustrates a block diagram of a predictive intervertebral disc degeneration system according to an aspect of the present disclosure.

FIG. 3 illustrates an intervertebral disc degeneration detection system 300 according to an aspect of the present disclosure. System 300 includes a predictive intervertebral disc degeneration detection engine 110, one or more medical devices 120, a notification engine 150, a clinical data record server 310, and one or more clinical applications 130.

Detection engine 110 is in communication with clinical data record server 310. Clinical data record server 310 is in communication with one or more medical devices 120 and one or more clinical applications 130. Detection engine 110 is also in communication with notification engine 150. In certain aspects, detection engine 110 is also in communication with one or more medical devices 120. In certain aspects, detection engine 110 is also in communication with one or more of the clinical applications 130.

In operation, clinical data record server 310 receives and stores clinical data from medical devices 120 and/or clinical applications 130. Detection engine 110 then processes the data to determine a prediction regarding the occurrence of an event. Based on the prediction, a notification is generated by notification engine 150.

In alternate aspects, clinical applications 130 may be, for example, an order entry application, a pharmacy application, a medication management application, an electronic medical record, and/or the like.

Clinical data record server 310 is adapted to receive and store clinical data from one or more medical devices 120 and/or clinical applications 130. Clinical data record server 310 may be part of, for example, a clinical information system, a healthcare information system, and/or a picture archiving and communication (PACS) system.

In an aspect, detection engine 110 is adapted to determine a prediction based at least in part on the clinical data in the clinical data record server 310. The prediction may be determined, for example, by a predictive algorithm as discussed above. Notification engine 150 is adapted to generate a notification based on the determined prediction from detection engine 110.

In certain aspects, detection engine 110 is adapted to receive clinical data directly from a clinical application 130. In certain aspects, detection engine 110 is adapted to receive clinical data directly from a medical device 120.

In certain aspects, the predictive algorithm is specified by the user using prediction definition tool 140 as described above.

Figure 4:
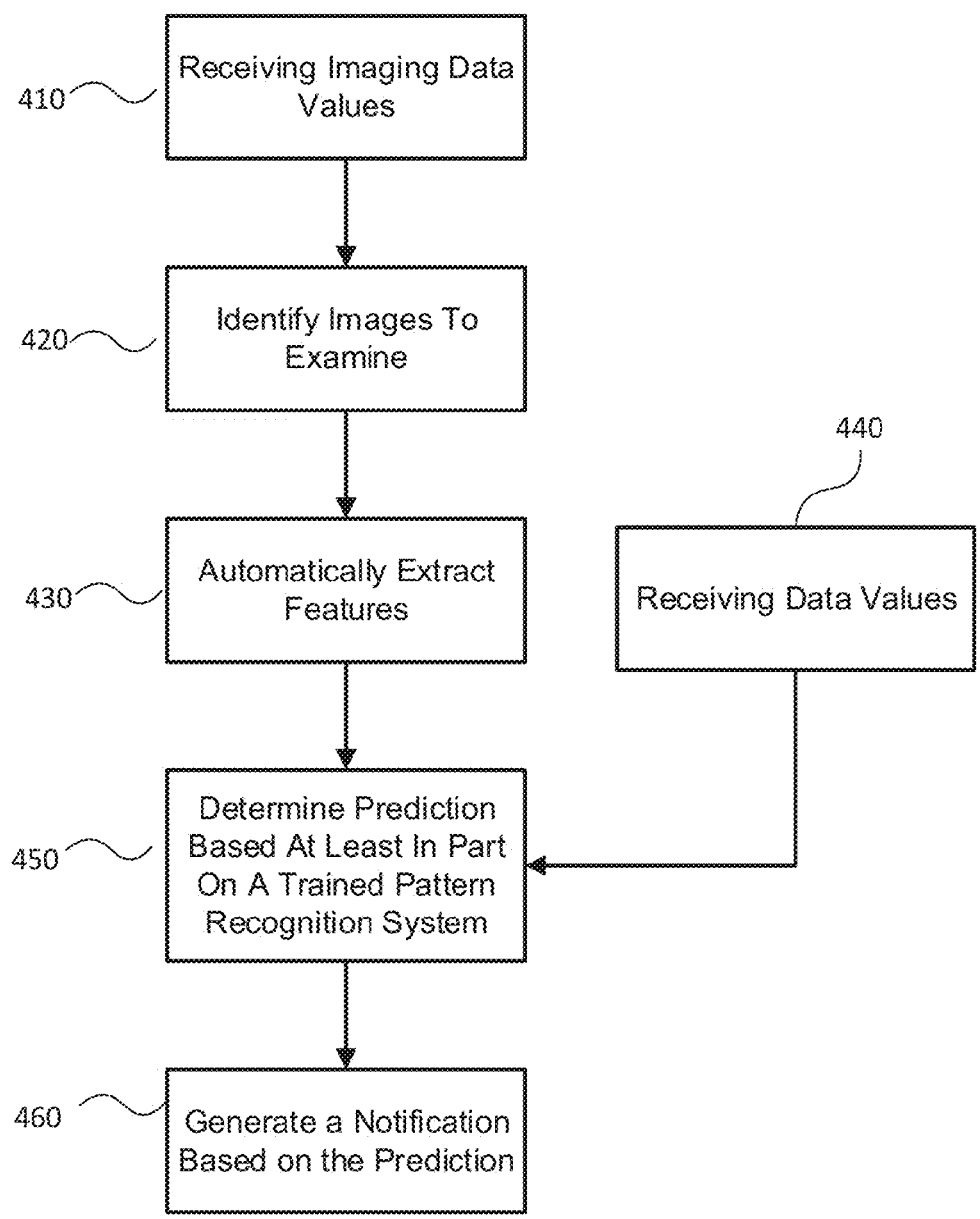
FIG. 4 illustrates a flow diagram for a method for predictive intervertebral disc degeneration according to an aspect of the present disclosure.

FIG. 4 is a flow diagram of predictive intervertebral disc degeneration detection process 400, according to an aspect of the disclosure.

At block 410, image data values are received. The data values may be a sequence of one or more parameters, for example. The data values may be received from a medical device similar to the medical device 120, discussed above, for example. In another example, the data values may be a sequence of medical images. The medical images may be received from a medical device 120, discussed above, for example.

At block 420, a sequence of images representing the desired area of the body to be examined are identified. In certain aspects, data from an imaging technique that can generate a sequence of images of the spinal region of a person are identified for examination.

At block 430, an automatic feature extraction module processes the sequence of images by segmenting the disc regions of the spine and automatically extracts texture features. These texture features may include one or more of the following: mean signal intensity (MSI), Contrast (C), Correlation (CO), Energy (E), Entropy (En) and Homogeneity (H) which can be quantified from the gray level co-occurrence matrix (GLCM) of the segmented disc region and are identified as individual biomarkers.

In certain aspects, these individual biomarkers are used alone and/or are combined into a prognostic combination marker by means of a weighted sum of the individual texture markers using linear discriminant analysis. The intervertebral disc degeneration detection engine may then use a predictive algorithm based on the combination marker predict the Intervertebral Disc loss over a certain amount of time using trained pattern recognition system 450. In certain aspects, the individual biomarkers and/or the prognostic combined markers may be used with additional data values from clinical information system, a healthcare information system and/or a picture archiving and communication system (PACS).

At block 440, clinical data values which may be relevant to the prediction are received. These data values may include information such as family history information, previous symptom information, or other medical data. In certain aspects, the data values include clinical data from a clinical application. The clinical application may be similar to the clinical application 130, discussed above, for example. In certain aspects, the data values are received from one or more clinical applications and/or medical devices. In certain aspects, the data values are received from a clinical data record server. In certain aspects, the clinical data record server is a picture archiving and communication system (PACS). The clinical data record server may be similar to the clinical data record server 310, discussed above, for example.

At block 450, in certain aspects, a prediction is determined based at least in part on the data values and/or the features extracted from the images and/or a trained pattern recognition system 110. In certain aspects, a prediction is determined based at least in part on the clinical data values and/or imaging data values, which may be useful for prediction of intervertebral disc loss. The data values received at blocks 410 and 440, discussed above, for example. The prediction may determine a trend based on one or more of the parameters. The predictive algorithm may utilize trending analysis and/or evaluating a trend over time, for example. The predictive algorithm may then determine that at some point in the future, the determined trend would indicate the occurrence of an event. Based on this determination, a notification may be provided.

In certain aspects, the predictive algorithm is specified by the user. For example, a user may utilize a prediction definition tool, similar to the prediction definition tool 140, discussed above, for example, to create a predictive algorithm.

In certain aspects, the prediction algorithm determines a prediction based at least in part on data for multiple parameters. The parameters may be from one or more medical devices, for example. In certain aspects, the prediction algorithm determines a prediction based at least in part on data from a clinical application. In certain aspects, the prediction algorithm determines a prediction based at least in part on data from multiple clinical applications. In certain aspects, the prediction algorithm determines a prediction based at least in part on data from a picture archiving and communication system (PACS). In certain aspects, the prediction algorithm determines a prediction based at least in part on data from at least one clinical application, one medical device, and one PACS system or a sub-combination of these systems.

At block 460, a notification may be generated depending on the prediction obtained in block 450. In certain aspects, the intervertebral disc degeneration detection engine 110 is adapted to generate a notification based on the determined prediction, 460, discussed above, for example. The notification may be generated by a notification engine similar to the notification engine 150, discussed above, for example. The notification may be generated by a notification component similar to the notification component 230 discussed above. The notification may be an email to a healthcare provider treating a patient, an alert inbox of a physician, a page, text message, telephone message and/or the like.

In certain aspects, the notification algorithm is specified by the user. For example, a user may utilize a notification definition tool 160, discussed above, for example, to create a notification algorithm.

Certain aspects of the present disclosure may omit one or more of these steps and/or perform the steps in a different order than the order listed. For example, some steps may not be performed in certain aspects of the present disclosure. As a further example, certain steps may be performed in a different temporal order, including simultaneously, than that listed above. Lastly, process 400 is described with reference to elements of systems 100 and 300 described above, but it should be understood that other implementations are possible.

Implementation

The components, elements, and/or functionality of the interface(s) and system(s) described above may be implemented alone or in combination in various forms in hardware, firmware, and/or a set of software instructions. Certain aspects may be provided as a set of instructions residing on a computer-readable medium, such as a memory or hard disk, for execution on a general purpose computer or other processing device, such as, for example, a PACS workstation or one or more dedicated processors.

One or more of the steps of the method may be implemented alone or in combination in hardware, firmware, and/or a set of instructions in software, for example. Certain aspects may be provided as a set of instructions residing on a computer-readable medium such as a memory, hard disk, DVD, or CD, for execution on a general purpose computer or other processing device.

Thus, certain aspects of the present disclosure provide systems and methods for a predictive intervertebral disc degeneration detection engine. Certain aspects provide prognostic information regarding intervertebral disc degeneration loss based on information from multiple sources. Certain aspects allow the prediction of a medical problem based on trends of the currently available variables. Certain aspects provide for user-defined notifications. Certain aspects of the present disclosure provide a technical effect of a predictive intervertebral disc degeneration detection engine. Certain aspects provide a technical effect of intervertebral disc degeneration detection based on information from multiple sources.

Certain aspects provide a technical effect of allowing the prediction of a medical problem based on trends of the currently available variables. Certain aspects provide a technical effect of user-defined notifications.

Several aspects are described above with reference to drawings. These drawings illustrate certain details of specific aspects that implement the systems and methods and programs of the present disclosure. However, describing the disclosure with drawings should not be construed as imposing on the disclosure any limitations associated with features shown in the drawings. The present disclosure contemplates methods, systems, and program products on any machine-readable media for accomplishing its operations. As noted above, the aspects of the present disclosure may be implemented using an existing computer processor, or by a special purpose computer processor incorporated for this or another purpose or by a hardwired system.

As noted above, certain aspects within the scope of the present disclosure include program products comprising machine-readable media for carrying or having machine-executable instructions or data structures stored thereon.

Figure 5:
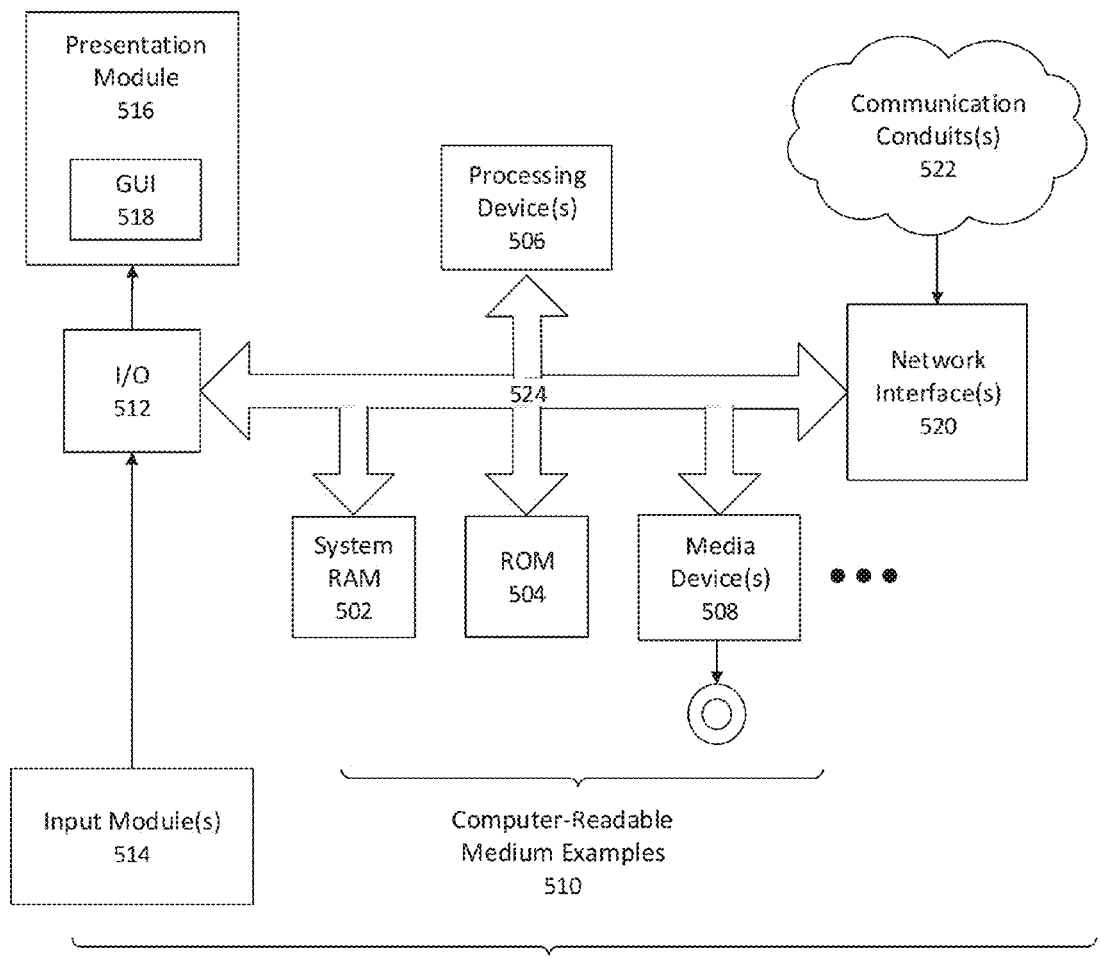
FIG. 5 shows a block diagram of an example processor system that can be used to implement systems and methods described herein.
Figure 5:
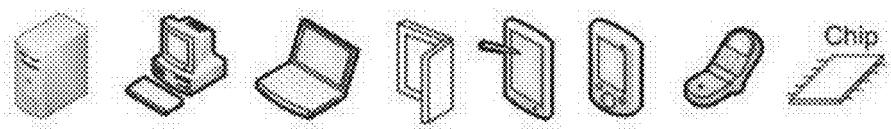

Referring now to FIG. 5, a block diagram illustrating an exemplary computer system useful for implementing the present disclosure is shown. That is FIG. 5 sets forth illustrative computing functionality 500 that may be used to implement any component of the systems (e.g., system 100 or 300) or any aspects of the functions (e.g., process 400) described herein. In all cases, computing functionality 500 represents one or more physical and tangible processing mechanisms.

Computing functionality 500 may include volatile and non-volatile memory, such as RAM 502 and ROM 504, as well as one or more processing devices 506 (e.g., one or more central processing units (CPUs), one or more graphical processing units (GPUs), and the like). Computing functionality 500 also optionally includes various media devices 508, such as a hard disk module, an optical disk module, and so forth. Computing functionality 500 can perform various operations identified above when the processing device(s) 506 executes instructions that are maintained by memory (e.g., RAM 502, ROM 504).

More generally, instructions and other information may be stored on any computer readable medium 510, including, but not limited to, static memory storage devices, magnetic storage devices, and optical storage devices. The term "computer readable medium" also encompasses plural storage devices. In all cases, computer readable medium 510 represents some form of physical and tangible entity. By way of example, and not limitation, computer readable medium 510 may comprise "computer storage media" and "communications media."

"Computer storage media" include volatile and non-volatile, removable and non-removable media implemented in any method or technology for storage of information, such as computer readable instructions, data structures, program modules or other data. Computer storage media include, but are not limited to, RAM 502, ROM 504, EEPROM, Flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

"Communication media" typically embody computer readable instructions, data structures, program modules, or other data in a modulated data signal, such as carrier wave or other transport mechanism. Communication media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media. Combinations of any of the above are also included within the scope of computer readable medium.

Computing functionality 500 also includes an input/output module 512 for receiving various inputs (via input modules 514), and for providing various outputs (via one or more output modules). One particular output mechanism may include a presentation module 516 and an associated GUI 518. Computing functionality 500 may also include one or more network interfaces 520 for exchanging data with other devices via one or more communication conduits 522. One or more communication buses 524 communicatively couple the above-described components together.

Communication conduit(s) 522 may be implemented in any manner (e.g., by a local area network, a wide area network (e.g., the Internet), etc., or any combination thereof). Communication conduit(s) 522 can include any combination of hardwired links, wireless links, routers, gateway functionality, name servers, etc., governed by any protocol or combination of protocols.

Alternatively, or in addition, any of the functions described herein can be performed, at least in part, by one or more hardware logic components. For example, without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The terms "module" and "component" as used herein generally represent software, firmware, hardware, or combinations thereof. In the case of a software implementation, the module or component represents program code that performs specified tasks when executed on a processor. The program code can be stored in one or more computer readable memory devices, as described with reference to FIG. 5. The features of the present disclosure described herein are platform-independent, meaning that the techniques can be implemented on a variety of commercial computing platforms having a variety of processors (e.g., desktop, laptop, notebook, tablet computer, personal digital assistant (PDA), mobile telephone, smart telephone, gaming console, and the like).

In some aspects, computing functionality 500 implements processes and methods described herein. In other aspects, presentation module presents screenshots, visual representations, and GUIs to the user as described herein.

CONCLUSION

The foregoing description of aspects of the disclosure has been presented for purposes of illustration and description. It is not intended to be exhaustive or to limit the disclosure to the precise form disclosed, and modifications and variations are possible in light of the above teachings or may be acquired from practice of the disclosure. The aspects were chosen and described in order to explain the principals of the disclosure and its practical application to enable one skilled in the art to utilize the disclosure in various aspects and with various modifications as are suited to the particular use contemplated.

Those skilled in the art will appreciate that the aspects disclosed herein may be applied to the formation of any healthcare information processing system. Certain features of the aspects of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter.

While the disclosure has been described with reference to certain aspects, it will be understood by those skilled in the art that various changes may be made and equivalents may be substituted without departing from the scope of this disclosure. In addition, many modifications may be made to adapt a particular situation or material to the teachings of the disclosure without departing from its scope. Therefore, it is intended that the disclosure not be limited to the particular aspect disclosed.

What is claimed is:

1. A computer-implemented method to predict intervertebral disc degeneration, the method comprising:
   receiving image data comprising one or more images of the human spine;
   segmenting, using a processor, disc regions of said one or more images;
   generating, using the processor, individual biomarkers based on texture features of said segmented disc regions;
   generating, using the processor, a prognostic marker from said individual biomarkers;
   wherein generating the prognostic marker comprises utilizing a weighted sum of individual texture biomarkers and linear discriminant analysis; and
   facilitating prediction of intervertebral disc loss based on the prognostic marker.

2. The computer-implemented method of claim 1, wherein intervertebral disc loss prediction is based at least in part on said prognostic marker and a trained pattern recognition system.

3. The computer-implemented method of claim 1, wherein the methods further comprises:
   receiving a sequence of data values for a parameter from a medical device; and
   intervertebral disc loss prediction is based at least in part on said prognostic marker, said individual biomarkers and said data values.

4. The computer-implemented method of claim 1, wherein intervertebral disc loss prediction is based at least in part on determination of a trend in the sequence of data values and prognostic markers.

5. The computer-implemented method of claim 1, wherein the method further comprises:
   generating a notification based on the prediction.

6. A non-transitory computer storage device including program instructions for execution by a computing device to perform:
   receiving image data comprising one or more images of the human spine;
   segmenting disc regions of said one or more images;
   generating individual biomarkers based on texture features of said segmented disc regions;
   generating a prognostic marker from said individual biomarkers;
   generating the prognostic marker by utilizing a weighted sum of individual texture biomarkers and linear discriminant analysis; and
   facilitating prediction of intervertebral disc loss based on the prognostic marker.

7. The computer storage device of claim 6, further including program instructions for execution by said computing device to perform:

intervertebral disc loss prediction based at least in part on said prognostic marker and a trained pattern recognition system.

8. The computer storage device of claim 6, further including program instructions for execution by said computing device to perform:
receiving a sequence of data values for a parameter from a medical device; and
intervertebral disc loss prediction based at least in part on said prognostic marker, said individual biomarkers and said data values.

9. The computer storage device of claim 6, further including program instructions for execution by said computing device to perform:
intervertebral disc loss prediction based at least in part on determination of a trend in the sequence of data values and prognostic markers.

10. The computer storage device of claim 6, further including program instructions for execution by said computing device to perform:
generating a notification based on the prediction.

11. A system comprising a processor, the processor configured to execute computer program instructions to:
receive image data comprising one or more images of the human spine;
segment disc regions of said one or more images;
generate individual biomarkers based on texture features of said segmented disc regions;
generate a prognostic marker from said individual biomarkers;
generating said prognostic marker utilizing a weighted sum of individual texture biomarkers and linear discriminant analysis; and
facilitate a prediction of intervertebral disc loss based on the prognostic marker.

12. The system of claim 11, wherein the system further comprises:
intervertebral disc loss prediction based at least in part on said prognostic marker and a trained pattern recognition system.

13. The system of claim 11, wherein the system further comprises:
receiving a sequence of data values for a parameter from a medical device; and
intervertebral disc loss prediction based at least in part on said prognostic marker, said individual biomarkers and said data values.

14. The system of claim 11, wherein the system further comprises:
intervertebral disc loss prediction based at least in part on determination of a trend in the sequence of data values and prognostic markers.

15. The system of claim 11, wherein the system further comprises:
generating a notification based on the prediction.

* * * * *